(12) United States Patent (10) Patent No.: US 9,055,900 B2
Yuasa (45) Date of Patent: Jun. 16, 2015

(54) SPECIMEN MEASUREMENT DEVICE AND SPECIMEN MEASUREMENT SYSTEM

(75) Inventor: Kazuhiro Yuasa, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 388 days.

(21) Appl. No.: 13/456,842

(22) Filed: Apr. 26, 2012

(65) Prior Publication Data

US 2012/0276843 A1   Nov. 1, 2012

(30) Foreign Application Priority Data

Apr. 26, 2011  (JP) ................................. 2011-097929
Feb. 7, 2012  (JP) ................................. 2012-023917

(51) Int. Cl.
*H04B 7/24* (2006.01)
*A61B 5/145* (2006.01)
*G06F 19/00* (2011.01)
*G01N 33/487* (2006.01)

(52) U.S. Cl.
CPC ........ *A61B 5/14532* (2013.01); *G06F 19/3406* (2013.01); *G06F 19/366* (2013.01); *G01N 33/48792* (2013.01)

(58) Field of Classification Search
CPC ... H04W 76/023; H04W 76/02; H04W 76/00; H04W 76/021; H04W 76/045; H04W 76/005; H04W 76/022; H04W 76/025; H04W 76/041; H04W 76/068
USPC .......................................................... 455/39
See application file for complete search history.

(56) References Cited

U.S. PATENT DOCUMENTS

| | | | |
|---|---|---|---|
| 6,503,191 B1 * | 1/2003 | Miller | 600/30 |
| 7,719,303 B2 | 5/2010 | Shiraki et al. | |
| 8,108,047 B2 * | 1/2012 | Schumann | 607/46 |
| 8,226,905 B2 * | 7/2012 | Abdallah | 422/404 |
| 8,265,887 B2 * | 9/2012 | Itou et al. | 702/45 |
| 8,318,096 B2 | 11/2012 | Okuda et al. | |
| 8,326,650 B2 * | 12/2012 | Horiguchi et al. | 705/3 |

(Continued)

FOREIGN PATENT DOCUMENTS

CN  1908668 A  2/2007
CN  201438187 U  4/2010

(Continued)

OTHER PUBLICATIONS

The European Search Report with mailing date of Aug. 9, 2012; EP Application No. 12 16 5586.

(Continued)

*Primary Examiner* — Andrew Wendell
*Assistant Examiner* — Maryam Soltanzadeh
(74) *Attorney, Agent, or Firm* — Studebaker & Brackett PC

(57) ABSTRACT

A specimen measurement system simplifies the function of a measurement device and facilitates measurement under an appropriate condition. Use is made of a specimen measurement device suitable for the system. The specimen measurement device includes a measurement unit, a measurement condition decision unit, and a communication unit. The measurement unit measures a specific component contained in the specimen. The measurement condition decision unit decides suitability of measurement conditions necessary for the measurement, and generates measurement condition data including decision result about the suitability of the measurement conditions. The communication unit transmits the measurement condition data through wireless communication.

9 Claims, 15 Drawing Sheets

(56) References Cited

U.S. PATENT DOCUMENTS

| | | | |
|---|---|---|---|
| 8,401,777 B2* | 3/2013 | Ryman | 701/123 |
| 8,556,630 B2* | 10/2013 | Hackett | 434/236 |
| 8,583,205 B2* | 11/2013 | Budiman et al. | 600/347 |
| 2007/0179356 A1 | 8/2007 | Wessel | |
| 2007/0188145 A1* | 8/2007 | Kim et al. | 320/132 |
| 2008/0058616 A1 | 3/2008 | Nakagawa et al. | |
| 2008/0076969 A1 | 3/2008 | Kraft et al. | |
| 2008/0300572 A1 | 12/2008 | Rankers et al. | |
| 2010/0035334 A1 | 2/2010 | Okuda et al. | |
| 2010/0137697 A1 | 6/2010 | Kubo et al. | |
| 2010/0159835 A1 | 6/2010 | Aoki et al. | |
| 2011/0075701 A1* | 3/2011 | Son | 374/100 |
| 2012/0179017 A1 | 7/2012 | Satou et al. | |

FOREIGN PATENT DOCUMENTS

| | | |
|---|---|---|
| EP | 0 387 630 A2 | 9/1990 |
| JP | 2002-368907 A | 12/2002 |
| JP | 2009523469 A | 6/2009 |
| JP | 2009198491 A | 9/2009 |
| JP | 2011064597 A | 3/2011 |
| WO | 2006/003919 A1 | 1/2006 |
| WO | 2008/136437 A1 | 11/2008 |
| WO | 2011/033876 A1 | 3/2011 |

OTHER PUBLICATIONS

An Office Action issued by the Korean Patent Office on Jul. 23, 2013, which corresponds to Korean Patent Application No. 10-2012-0043505 and is related to U.S. Appl. No. 13/456,842.

The first Office Action issued by the Chinese Patent Office on Mar. 31, 2014, which corresponds to Chinese Patent Application No. 201210126181.3 and is related to U.S. Appl. No. 13/456,842.

* cited by examiner

SPECIMEN MEASUREMENT DEVICE AND SPECIMEN MEASUREMENT SYSTEM

BACKGROUND OF THE INVENTION

1. Field of the Invention

The present invention relates to a specimen measurement device and a specimen measurement system.

2. Description of the Related Art

FIG. 15 illustrates an example of existing specimen measurement systems (see, for example, JP-A1-2008-136437). The specimen measurement system 900 includes a specimen measurement device 91 and a personal computer 93. The specimen measurement device 91 is a device for self-monitoring of blood glucose (hereinafter, SMBG) to be used by, for example, a diabetes patient to measure his/her own blood sugar level. To perform the measurement, the patient inserts a sensor piece 92 into the specimen measurement device 91 and applies a droplet of blood onto the sensor piece 92. The measurement data obtained by the specimen measurement device 91 is transmitted to the personal computer 93 through the cable 94, to be stored therein. The measurement data can be utilized for example by a physician to perform treatment and medication suitable for the condition of the patient.

Recently, specimen measurement devices with a simplified structure have been developed, in response to requirement for cost reduction, for example as disclosed in JP-A1-2006-003919. In the specimen measurement device 91, 7-segment digits 91b are adopted for display so as to simplify the display screen 91a. The display screen 91a is designed so as to also display a symbol 91c, which is relatively small and simple.

In the specimen measurement device 91, when the device is in an error state such as battery run out, the symbol 91c is displayed as an alert to that effect. However, the symbol 91c is unremarkable and hence prone to be overlooked by the user. Especially, the diabetes patients often have weakened vision, and therefore such a display is often overlooked.

Accordingly, it is desirable that the error display is shown at an earliest possible stage. For example, if the error display appeared after the patient collected the blood, the sensor piece 92 would have to be wasted, and besides the patient would suffer a physical stress originating from the loss of blood.

In the case where the measurement system it to be utilized, the user has to connect the specimen measurement device 91 and the personal computer 93 with the cable 94, which is a considerable trouble to the user.

SUMMARY OF THE INVENTION

The present invention has been proposed in view of the foregoing situation, and provides a specimen measurement device and a specimen measurement system having a simplified structure and yet capable of conducting the user so as to perform the measurement under an appropriate condition.

In an aspect, the present invention provides a specimen measurement device including a measurement unit for measurement of a specific component contained in a specimen, a measurement condition decision unit that decides suitability of at least one measurement condition required for the measurement and generates measurement condition data containing a decision result on the suitability of the measurement condition, and a data transmitter that transmits the measurement condition data through wireless communication.

Preferably, the specimen measurement device may further include a temperature measurement unit that measures a temperature of a place related to the measurement of the specimen, and the measurement condition decision unit may decide suitability of the temperature measured by the temperature measurement unit with respect to the measurement of the specimen, and add the decision result to the measurement condition data as temperature suitability data.

Preferably, the specimen measurement device may further include a charge storage unit and a charge amount measurement unit that measures a charge amount in the charge storage unit, and the measurement condition decision unit may decide suitability of the charge amount measured by the charge amount measurement unit with respect to the measurement of the specimen, and add the decision result to the measurement condition data as charge amount suitability data.

Preferably, the specimen measurement device may further include a date and time generation unit having a clock function so as to identify a date and time of the measurement, and the measurement condition decision unit may decide suitability of a time-counting status of the clock function of the date and time generation unit with respect to the measurement of the specimen, and add the decision result to the measurement condition data as time-counting status suitability data.

Preferably, insertion of a sensor piece spotted with the specimen into the specimen measurement device may activate the specimen measurement device to measure the specimen.

Preferably, the specific component may be blood sugar.

Preferably, the specimen measurement device may include a sensor piece detector that detects insertion and removal of the sensor piece, and the specimen measurement device may be switched, when the sensor piece detector detects the insertion of the sensor piece, to an operative state in which the specimen can be measured from a stand-by state in which the specimen is unable to be measured.

Preferably, the measurement condition decision unit may automatically decide the suitability of the measurement condition, after the sensor piece is inserted.

Preferably, the data transmitter may automatically transmit the measurement condition data after the measurement condition decision unit decides the suitability of the measurement condition.

Preferably, the data transmitter may automatically establish wireless communication after the sensor piece is inserted and before the measurement condition data is transmitted.

Preferably, the specimen measurement device may include a measurement device-end display unit that displays at least one of the measurement result of the measurement unit and the decision result of the measurement condition decision unit.

In an embodiment, the specimen measurement device may not be provided with any function to display the measurement result given by the measurement unit and the decision result given by the measurement condition decision unit.

In another aspect, the present invention provides a specimen measurement system including the foregoing specimen measurement device, and a communication apparatus including a data receiver that receives, through wireless communication, the measurement condition data transmitted from the data transmitter of the specimen measurement device and a communication apparatus-end display unit that displays measurement condition information based on the measurement condition data.

Preferably, the communication apparatus may include an improvement remedy storage unit in which improvement remedy data for improving a status of the specimen measurement device on the basis of the measurement condition data is stored, and the communication apparatus-end display unit may display the improvement remedy data together with or after a display of the measurement condition information.

Preferably, measurement data generated by the measurement unit may be transmitted from the specimen measurement device by the data transmitter, and the measurement data received by the data receiver may be displayed on the communication apparatus-end display unit in the communication apparatus.

With such a configuration, in the case where the status of the specimen measurement device is not suitable for performing the measurement, the communication apparatus outputs the information to that effect. Accordingly, the user is more likely to notice that the status of the specimen measurement device is not suitable for the measurement, than in the case where, for example, such information is only outputted on the specimen measurement device. Consequently, the user can be prevented from performing the measurement under an environment unsuitable for making a decision for treatment or medication.

Other features and advantages of the present invention will become more apparent through the detailed description given below with reference to the accompanying drawings.

DETAILED DESCRIPTION OF THE PREFERRED EMBODIMENTS

Preferred embodiments of the present invention will be described below with reference to the drawings.

Figure 1:
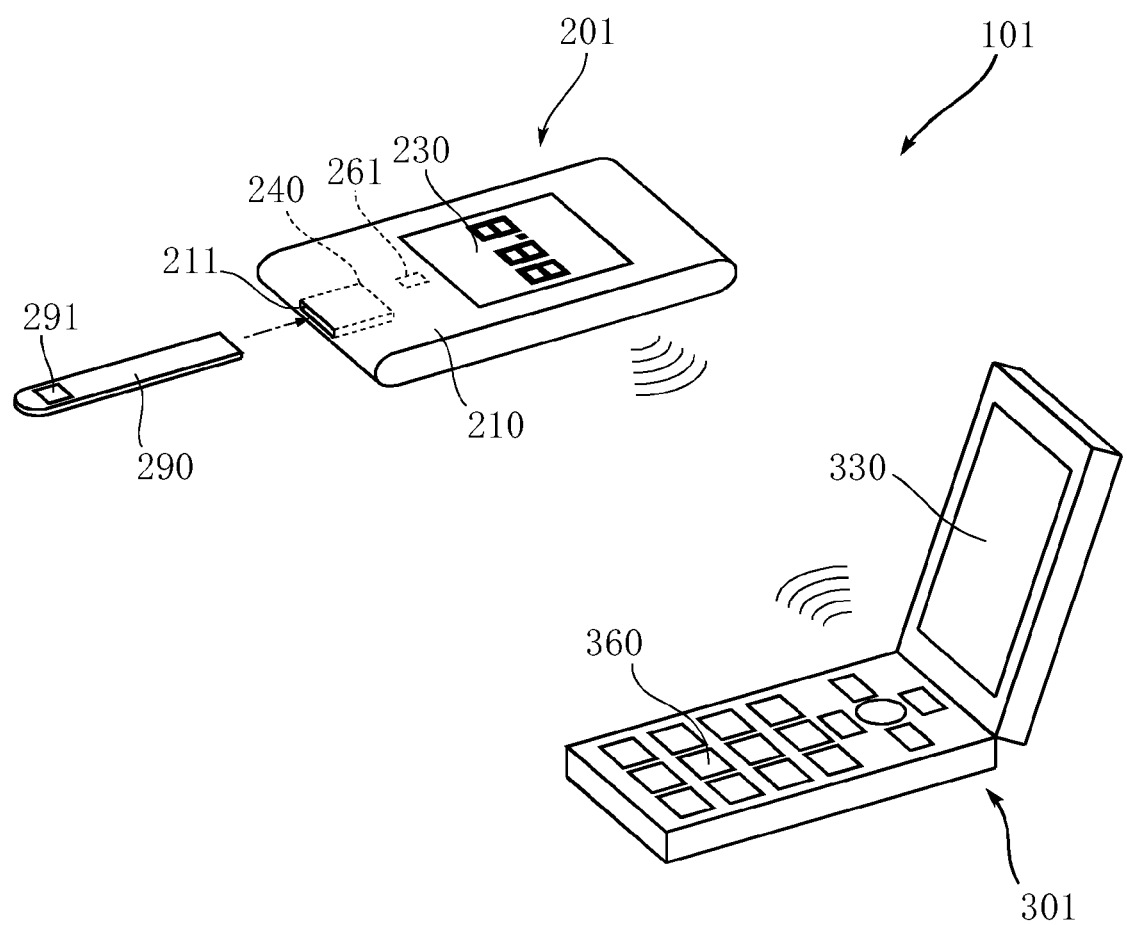
FIG. 1 is a perspective view showing a specimen measurement device according to a first embodiment of the present invention and a specimen measurement system including the specimen measurement device.

FIG. 1 illustrates a specimen measurement device according to a first embodiment of the present invention, and a specimen measurement system that includes the specimen measurement device. The specimen measurement system 101 shown in FIG. 1 includes a specimen measurement device 201 and a communication apparatus 301.

Figure 2:
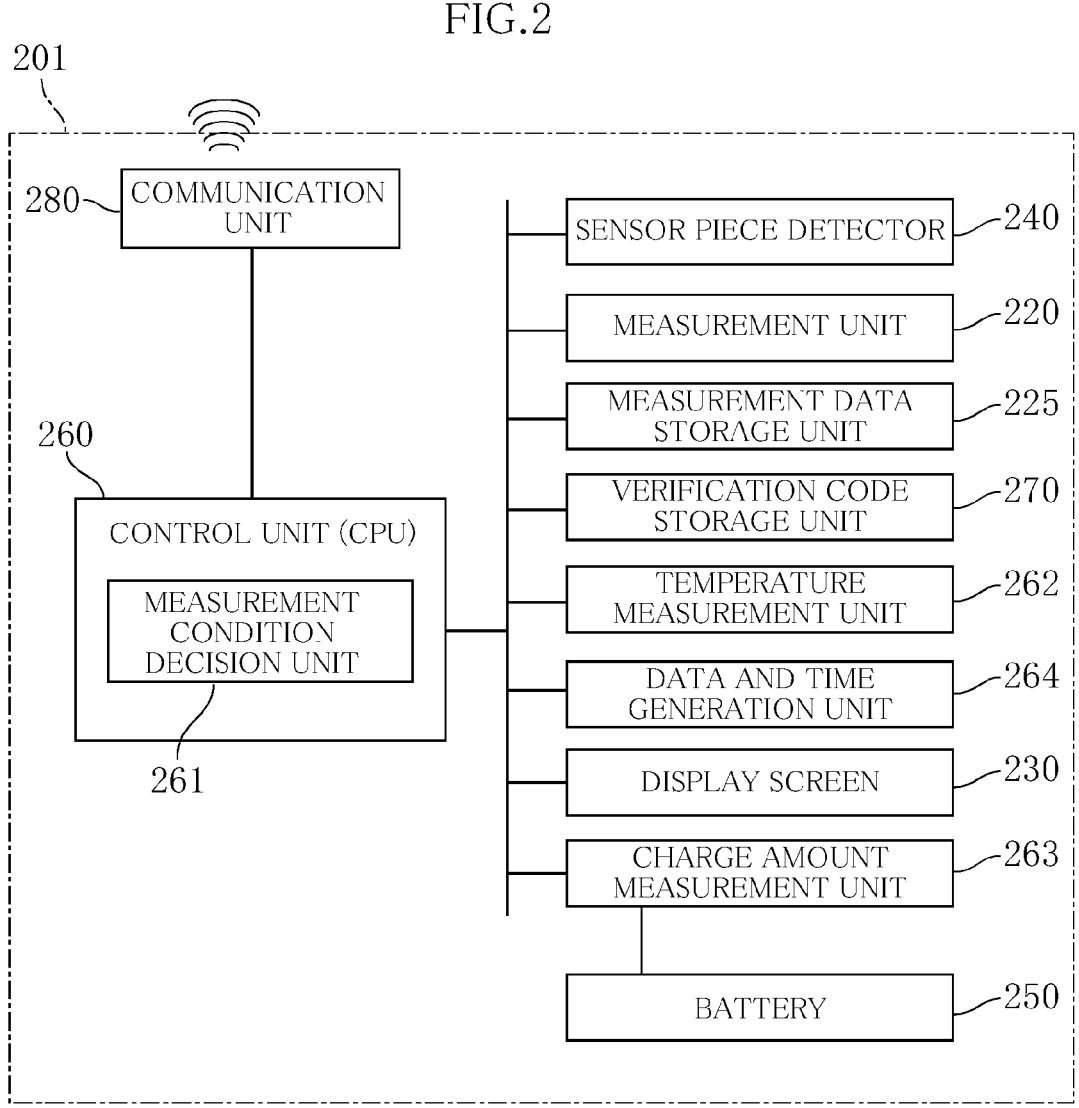
FIG. 2 is a block diagram showing a configuration of the specimen measurement device.

The specimen measurement device 201 exemplifies a SMBG device used for self measurement of the user's own blood sugar level. As shown in FIGS. 1 and 2, the specimen measurement device 201 includes a case 210, a measurement unit 220, a measurement data storage unit 225, a display screen 230, a sensor piece detector 240, a battery 250, a control unit 260, a temperature measurement unit 262, a charge amount measurement unit 263, a date and time generation unit 264, and a communication unit 280. To perform the measurement with the specimen measurement device 201, a sensor piece 290 is employed. The sensor piece 290 includes a spotting section 291. To perform the measurement, the sensor piece 290 is inserted into the specimen measurement device 201. A droplet of the blood of the user is applied to the spotting section 291.

The case 210 is formed of a resin for example, and defines the outer shape of the specimen measurement device 201. The case 210 includes an insertion slot through which the sensor piece 290 is to be inserted. The sensor piece detector 240 located inside the case 210 at a position spaced by a predetermined distance from the insertion slot 211, and serves to detect the insertion of the sensor piece 290. The sensor piece detector 240 may be realized in various manners. As a mechanical structure, a lever may be provided inside the case, so that the insertion is detected when the sensor piece 290 displaces the lever. As an electrical arrangement, a pair of electrodes may be provided inside the case, so that upon inserting the sensor piece 290 the electrodes become electrically connected thus to detect the insertion.

Figure 6:
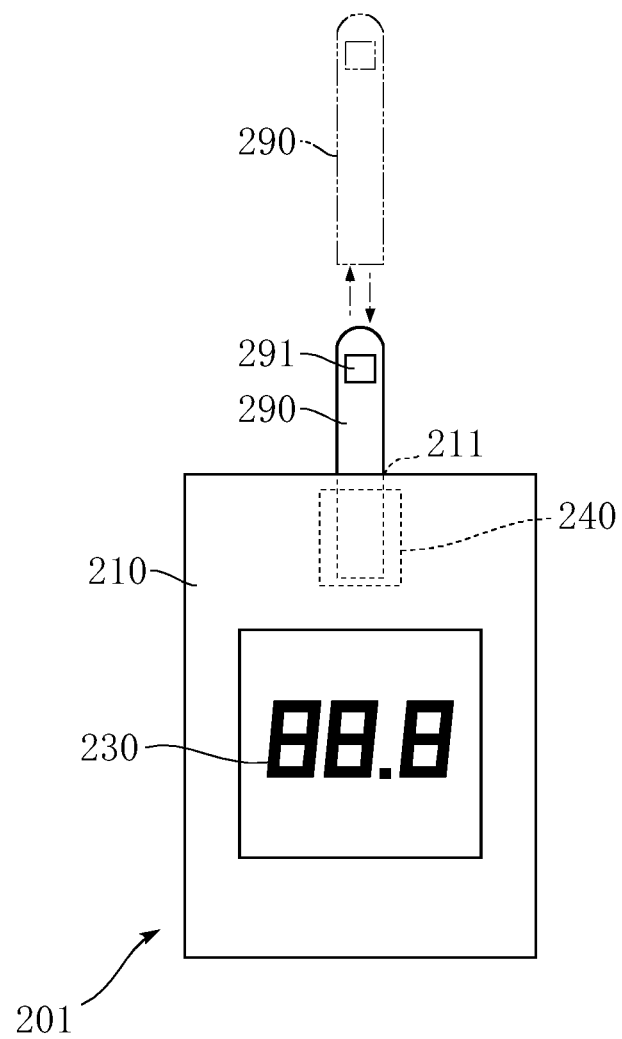
FIG. 6 is a front view showing insertion and removal of a sensor piece into and from the specimen measurement device.

The measurement unit 220 measures the blood sugar level. The measurement unit 220 includes a terminal electrically conductive with the sensor piece 290 with a droplet of blood applied to the spotting section 291, so as to electrically measure the blood sugar level. The measurement data storage unit 225 is for example constituted of a memory, and stores therein measurement data acquired by the measurement unit 220. The display screen 230 is constituted of an LCD for example, and displays the measurement data and other data. The display screen 230 is an example of the measurement device-end display unit according to the present invention. As shown in FIGS. 1 and 6, a 7-segment display is adopted in the display screen 230 in this embodiment, and a plurality of digits and letters can be displayed on the display screen 230. The battery 250 is an example of the charge storage unit according to the present invention, and serves as a power source for driving the specimen measurement device 201.

The control unit 260 controls the functional units of the specimen measurement device 201 in the measurement operation, and is constituted of a CPU, for example. In this embodiment, the control unit 260 includes the measurement condition decision unit 261. The measurement condition decision unit 261 decides whether measurement conditions of the specimen measurement device 201 are suitable in the light of predetermined criteria, and generates measurement condition data (subsequently described) on the basis of the decision. The temperature measurement unit 262 measures the temperature of a portion of the specimen measurement device 201 in the vicinity of the sensor piece 290, when the measurement is to be performed with the specimen measurement device 201. The charge amount measurement unit 263 measures the charge amount of the battery 250. The date and time generation unit 264 has a clock function, and generates date and time data including the information of date and time that the measurement unit 220 has performed the measurement.

The communication unit 280 is an example of the data transmitter according to the present invention, and performs transmission and reception of data through wireless communication. In this embodiment, the communication unit 280 performs communication in compliance with a predetermined wireless communication standard, for example Bluetooth (registered trademark). Accordingly, the communication unit 280 is capable of performing bi-directional wireless communication.

Figure 3:
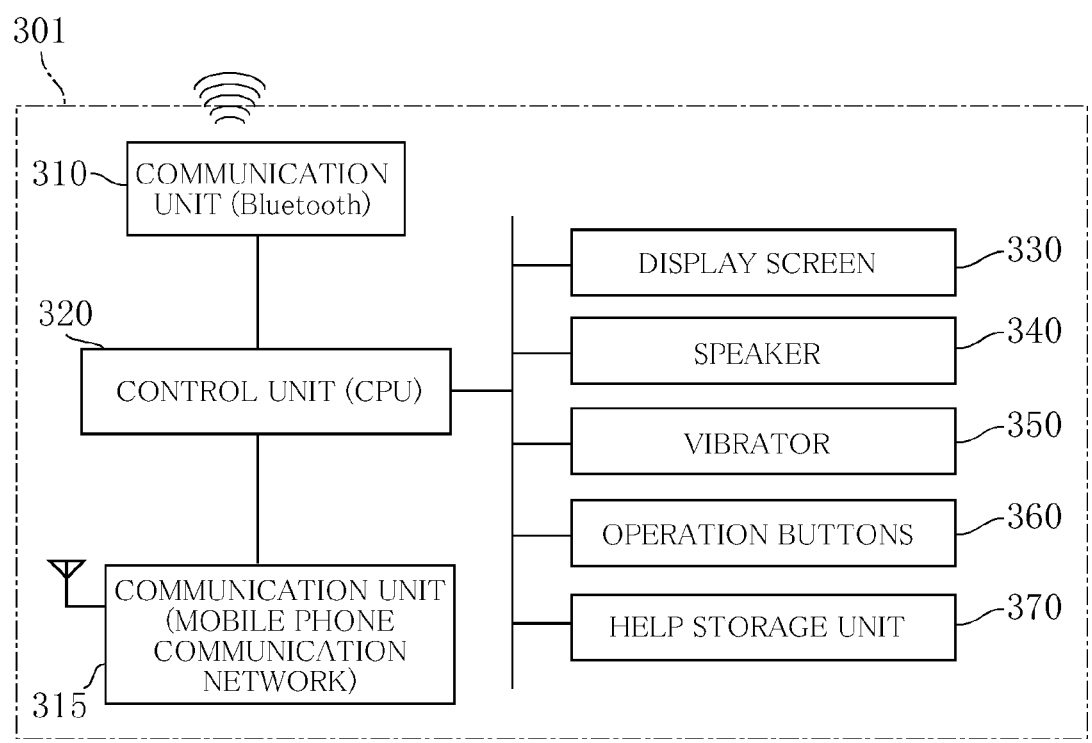
FIG. 3 is a block diagram showing a configuration of a communication apparatus employed in the specimen measurement system.

The communication apparatus 301 is for example a mobile phone, and receives the measurement data transmitted from the specimen measurement device 201 stores that data therein. The communication apparatus 301 is also capable of transmitting the received measurement data to a server apparatus through a public communication network. As shown in FIGS. 1 and 3, the communication apparatus 301 includes a first communication unit 310, a second communication unit 315, a control unit 320, a display screen 330, a speaker 340, a vibrator 350, operation buttons 360, and a help storage unit 370.

The communication unit 310 is an example of the data receiver according to the present invention, and performs transmission and reception of data through wireless communication. In this embodiment, the communication unit 310 performs communication in compliance with a predetermined wireless communication standard, for example Bluetooth (registered trademark). Accordingly, the communication unit 310 is capable of performing bi-directional wireless communication. The communication unit 315 serves for making access to the mobile phone communication network through wireless communication. Accordingly, the communication apparatus 301 is capable of accessing to the mobile phone communication network, and to the internet therethrough.

The control unit 320 controls the functional units of the communication apparatus 301 in the communication operation, and is constituted of a CPU, for example. The display screen 330 is an example of the communication apparatus-end display unit according to the present invention, and for example constituted of an LCD panel. The speaker 340 outputs voices in verbal communication, key tones, alarms, and so on. The operation buttons 360 include dial keys and directional keys. The vibrator 350 includes, for example, a micro motor and serves to vibrate the entirety of the communication apparatus 301.

The help storage unit 370 is an example of the improvement remedy storage unit according to the present invention, and constituted of a memory, for example. The help storage unit 370 contains improvement remedies applicable to errors with respect to each of the measurement conditions of the specimen measurement device 201.

Referring now to FIGS. 4 through 12, an operation of the specimen measurement device 201 and the specimen measurement system 101 will be described hereunder.

Figure 4:
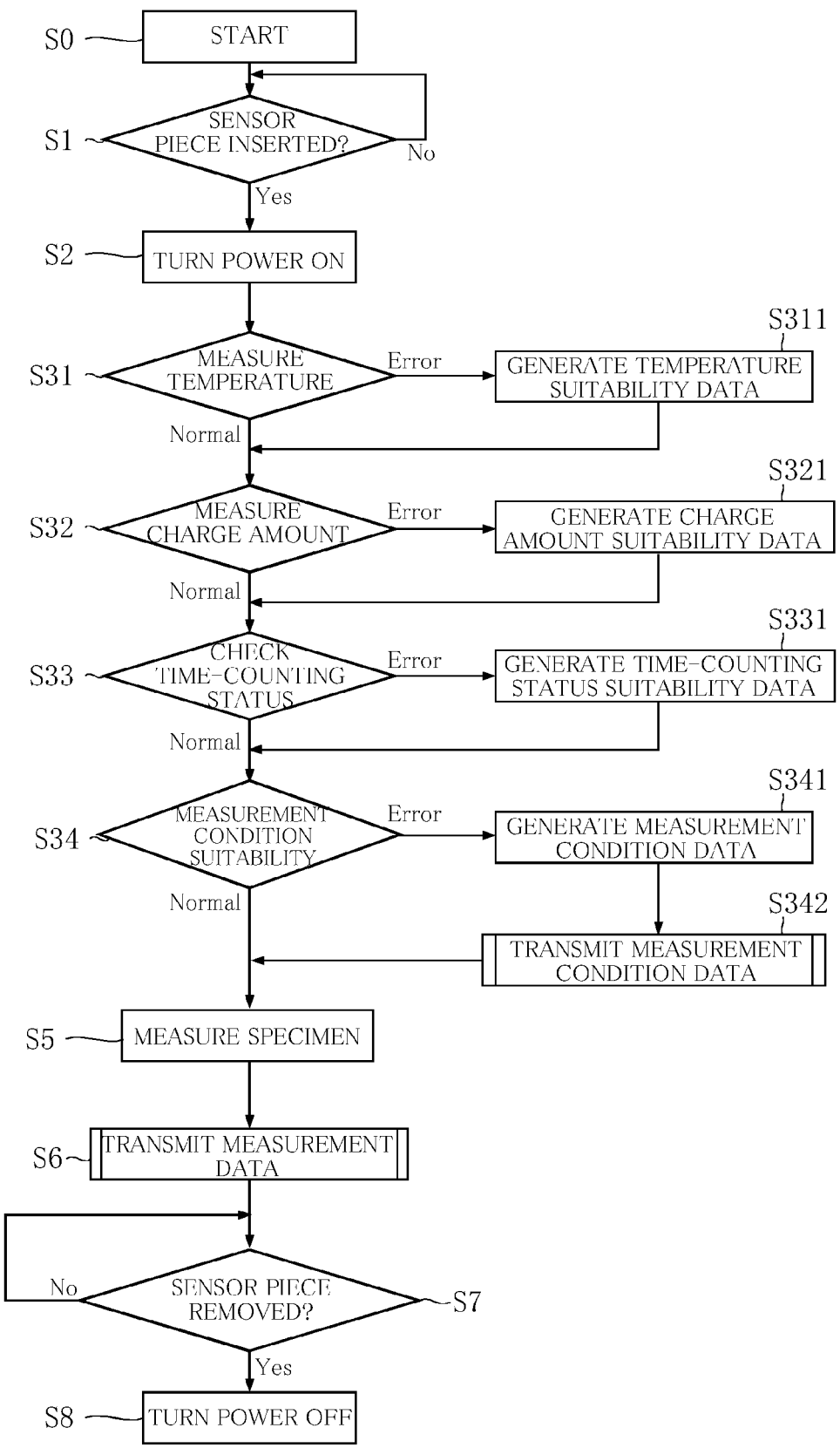
FIG. 4 is a flowchart showing an operation of the specimen measurement device.

FIG. 4 is a flowchart showing an operation of the specimen measurement device 201. A step S0 represents the start of the operation of the specimen measurement device 201. At a step S1, the power for the specimen measurement device 201 is still off and the display screen 230 is displaying nothing. At this step, however, the sensor piece detector 240 is capable of detecting the sensor piece 290. In the case where the sensor piece detector 240 is set to electrically detect the sensor piece 290, power is supplied to the sensor piece detector 240 at this stage. In the case where works without electricity, the sensor piece detector 240 may be completely disconnected from the power supply from the battery 250. Such a state, in which the power supply is off and yet the sensor piece detector 240 is ready for detecting the sensor piece 290, will hereinafter be referred to as "stand-by state".

At the step S1, it is decided whether the sensor piece 290 has been inserted, with the sensor piece detector 240. When the sensor piece 290 is inserted as shown in FIG. 6, an insertion detection signal is transmitted from the sensor piece detector 240 to the control unit 260 in FIG. 2. Then the control unit 260 instructs the battery 250 to supply power to the overall system of the specimen measurement device 201. At this point, the power for the specimen measurement device 201 is turned on at a step S2 as shown in FIG. 4. Such a state will hereinafter be referred to as "operative state".

After the power is turned on, steps S31, S32, and S33 are performed. At the step S31, the temperature measurement unit 262 measures the temperature, and the measured temperature is transmitted to the control unit 260. The measurement condition decision unit 261 in the control unit 260 decides whether the measured temperature is within a predetermined temperature range suitable for the measurement. In the case where the measured temperature is not within the temperature range, the measurement condition decision unit 261 decides that the temperature condition is an error, and generates temperature suitability data at a step S311. The temperature suitability data contains information that the measured temperature is not suitable for the measurement. Then the operation proceeds to the step S32 through the step S311, or in the case where the measured temperature is decided to be within the predetermined temperature range.

At the step S32, the charge amount measurement unit 263 checks the charge amount of the battery 250, and the charge amount is transmitted to the control unit 260. The measurement condition decision unit 261 in the control unit 260 compares the charge amount with a predetermined lower limit of the charge amount. In the case where the charge amount is below the charge amount lower limit, the measurement condition decision unit 261 decides that the charge amount is an error, and generates charge amount suitability data at a step S321. The charge amount suitability data contains information that the charge amount is insufficient for the measurement. Then the operation proceeds to the step S33 through the step S321, or in the case where the charge amount is decided to be higher than the lower limit.

At the step S33, the measurement condition decision unit 261 checks the time-counting status of the date and time generation unit 264. In the case where the date and time generation unit 264 is normally working the status is decided to be normal, and if the time-counting operation of the date and time generation unit 264 is stopped the status is decided as an error. In the latter case, the measurement condition decision unit 261 generates time-counting status suitability data at a step S331. The time-counting status suitability data contains information that the date and time generation unit 264 is not counting the time. Then the operation proceeds to the step S34 through the step S321, or in the case where the time-counting status is decided to be normal.

At the step S34, it is decided whether an error decision has been made at any one of the steps S31, S32, and S33. In the case where an error decision has been made at any one of the steps S31, S32, and S33, a step S341 is performed. At the step S341, measurement condition data is generated on the basis of one or more of the temperature suitability data, the charge amount suitability data, and the time-counting status suitability data actually generated through any one of the steps S311, S321, and S331. The measurement condition data contains information indicating which of the measurement conditions has been decided to be an error. Here, the temperature suitability data, the charge amount suitability data, and the time-counting status suitability data may contain information indicating whether the relevant condition is suitable or unsuitable, and the measurement condition data may contain, with respect to all of the temperature suitability data, the charge amount suitability data, and the time-counting status suitability data, information indicating whether the relevant condition is suitable or unsuitable. Then the communication unit 280 transmits the measurement condition data at a step S342. In this embodiment, the measurement condition data is transmitted through wireless communication in compliance with a predetermined wireless communication standard such as Bluetooth (registered trademark), to the communication apparatus 301.

In the case where the measurement conditions are decided to be suitable, the measurement unit 220 performs the blood sugar level measurement at a step S5. The acquired measurement data of blood sugar level is stored in the measurement data storage unit 225. At a step S6, the communication unit 280 transmits the blood sugar level measurement data to the communication apparatus 301. Such transmission may be automatically performed on the premise that the communication between the specimen measurement device 201 and the communication apparatus 301 has been established, or may be performed by the user's selective operation. Then when the sensor piece detector 240 detects the removal of the sensor piece 290 at a step S7, the power for the specimen measurement device 201 is turned off at a step S9.

Figure 5:
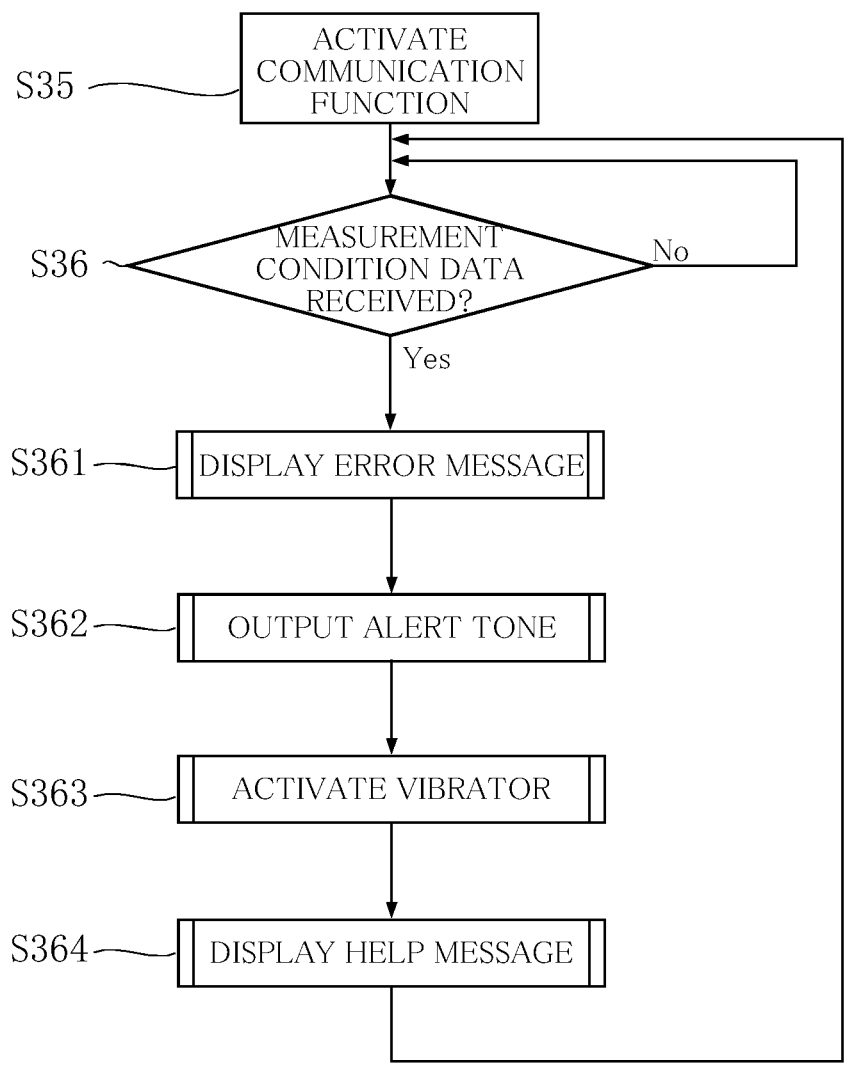
FIG. 5 is a flowchart showing an operation of the communication apparatus.

FIG. 5 is a flowchart showing an operation of the communication apparatus 301. Upon being set operable at a step S35, the communication apparatus 301 becomes ready to receive the measurement condition data from the specimen measurement device 201, at a step S36. When the measurement condition data is transmitted at the step S342 described referring to FIG. 4, the communication unit 310 of the communication apparatus 301 receives the measurement condition data at a step S36. The control unit 320 reads out the suitability information of the respective measurement conditions from the measurement condition data. Then the control unit 320 recognizes which of the measurement conditions was unsuitable (error), and displays an error message at a step S361.

Figure 7:
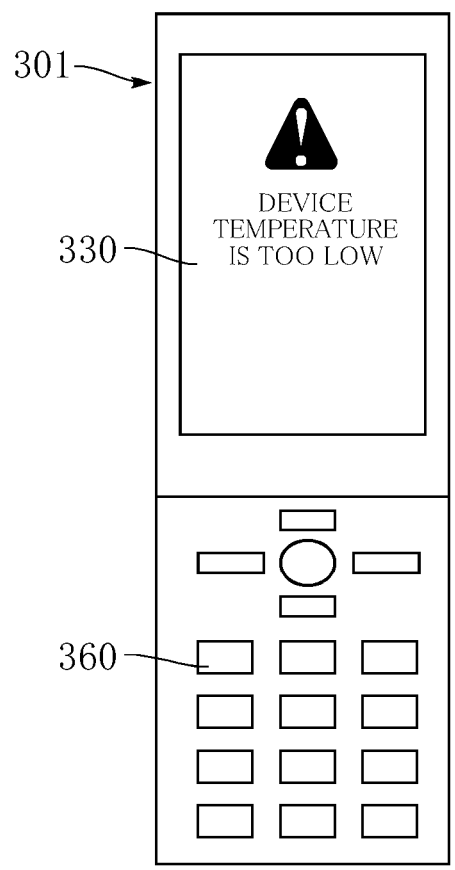
FIG. 7 is a front view showing an example of error messages displayed on the communication apparatus.
Figure 9:
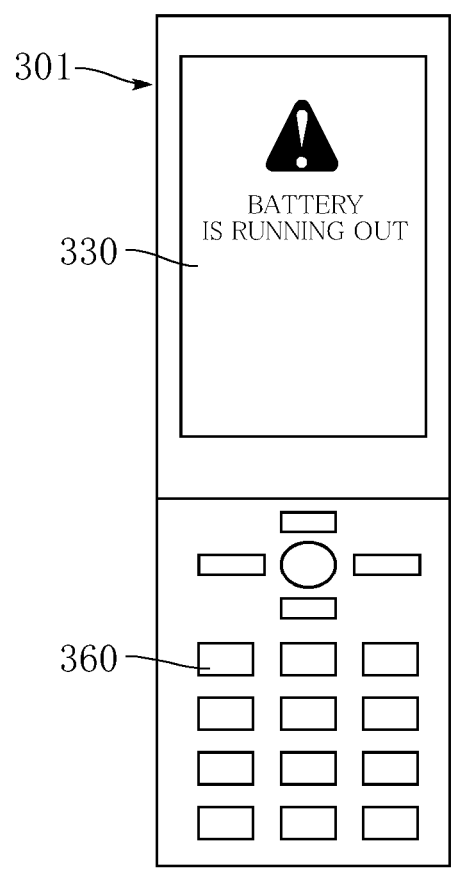
FIG. 9 is a front view showing another example of error messages displayed on the communication apparatus.
Figure 11:
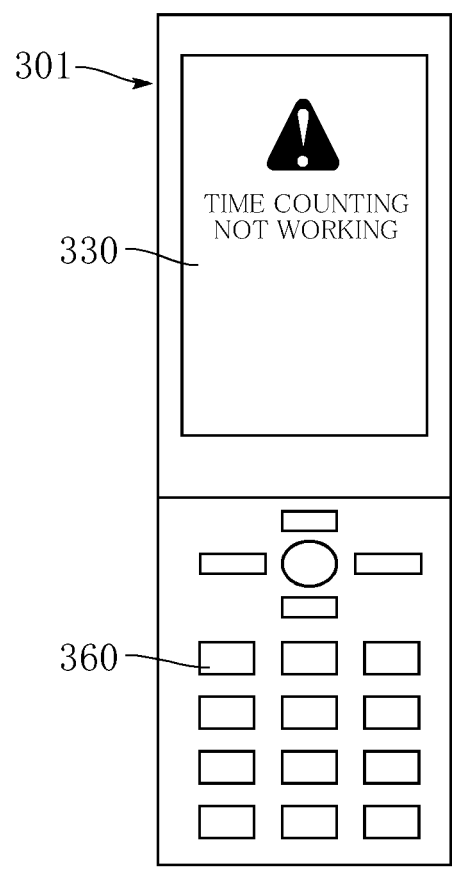
FIG. 11 is a front view showing still another example of error messages displayed on the communication apparatus.

More specifically, in the case where the temperature measured by the temperature measurement unit 262 was lower than the predetermined lower limit, an error message to that effect is displayed on the display screen 330, as shown in FIG. 7. Likewise, in the case where the charge amount measured by the charge amount measurement unit 263 was less than a predetermined lower limit of the charge amount, an error message to that effect is displayed on the display screen 330, as shown in FIG. 9. Further, in the case where the time-counting operation of the date and time generation unit 264 was stopped, an error message to that effect is displayed on the display screen 330, as shown in FIG. 11.

Once the error message is displayed at the step S361, the speaker 340 outputs an alert tone at a step S362. In addition, the vibrator 350 oscillates so as to vibrate the entirety of the communication apparatus 301 at a step S363. In the case where the communication apparatus 301 is set in a manner mode adopted in popular mobile phones, the step S362 may be skipped.

The alert tone and the vibration can be stopped, for example when the user presses any one of the operation buttons 360. Then at a step S364, a help message is displayed on the display screen 330. The help message corresponds to the measurement condition decided to be an error, selected by the control unit 320 from those stored in the help storage unit 370.

Figure 8:
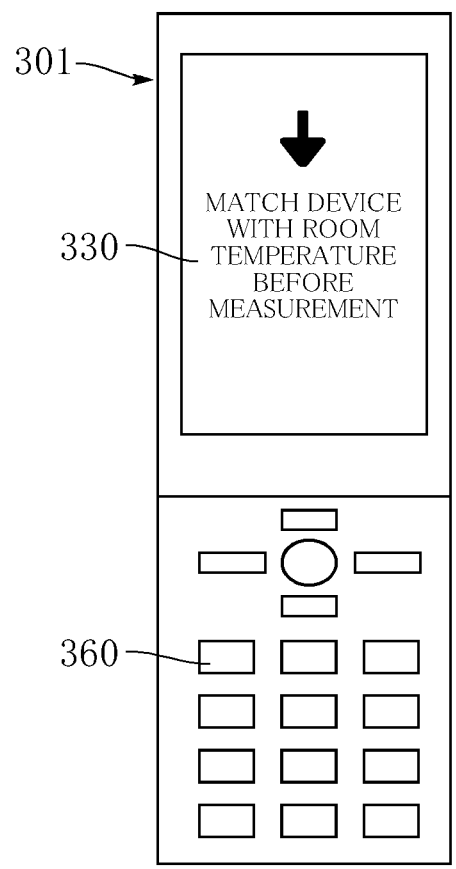
FIG. 8 is a front view showing an example of help messages displayed on the communication apparatus.
Figure 10:
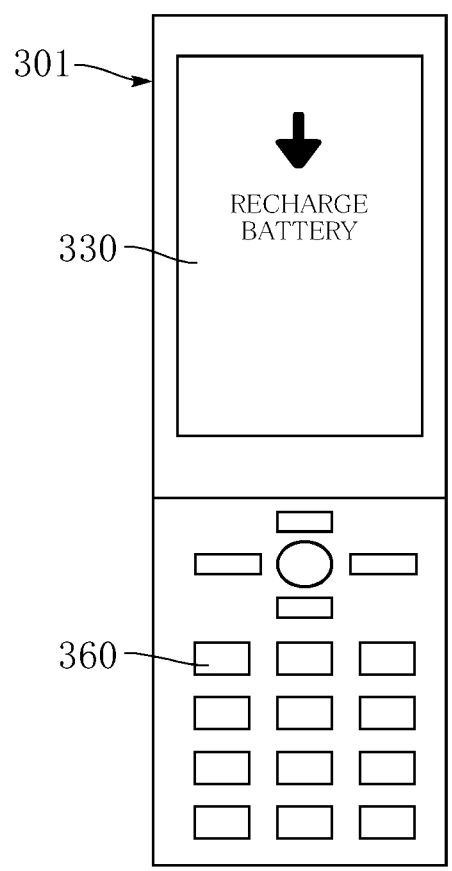
FIG. 10 is a front view showing another example of help messages displayed on the communication apparatus.
Figure 12:
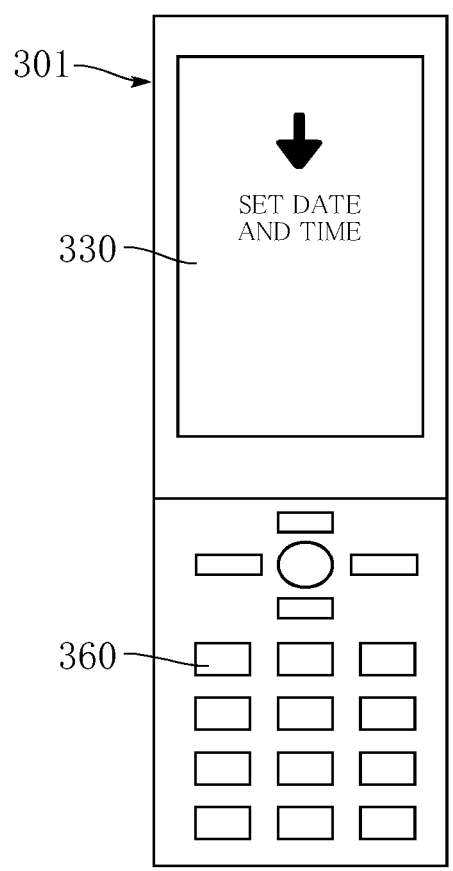
FIG. 12 is a front view showing still another example of help messages displayed on the communication apparatus.

More specifically, in the case where the error message shown in FIG. 7 is displayed because the temperature measured by the temperature measurement unit 262 was lower than the predetermined lower limit, a remedy for improving the temperature condition is displayed on the display screen 330, as shown in FIG. 8. Likewise, in the case where the error message shown in FIG. 9 is displayed because the charge amount measured by the charge amount measurement unit 263 was less than a predetermined lower limit of the charge amount, a message urging the user to recharge the battery 250 is displayed as shown in FIG. 10. Further, in the case where the error message shown in FIG. 11 is displayed because the time-counting operation of the date and time generation unit 264 was stopped, a message urging the user to set the date and time to thereby activate the time-counting function is displayed on the display screen 330, as shown in FIG. 12. It is desirable that the user perform the specimen measurement of the step S5 in FIG. 4, after performing the operation in accordance with such help messages.

The specimen measurement device 201 and the specimen measurement system 101 provide the following advantageous effects.

According to this embodiment, in the case where the status of the specimen measurement device 201 is not suitable for performing the measurement, the communication apparatus 301 outputs the information to that effect. Therefore, the user is more likely to notice that the status of the specimen measurement device is not suitable for the measurement, than in the case where, for example, such information is only outputted on the specimen measurement device 201. Such an arrangement prevents the user from performing the measurement under an environment unsuitable for making a decision for treatment or medication.

Since the communication apparatus 301 is a mobile phone, the user is most likely to carry the communication apparatus 301 with him/her when the user is about to perform the measurement with the specimen measurement device 201. Therefore, it is hopeful that the user promptly notices the error display outputted by the communication apparatus 301. In general, the display screen 330 of the communication apparatus 301 realized as a mobile phone is larger in size and capable of displaying a greater number of colors, than the display screen 230 of the specimen measurement device 201. This further assures that the user recognizes the error display outputted by the communication apparatus 301. Utilizing the display screen 330 of the communication apparatus 301 for the error display eliminates the need to prepare the function and region to display the error in the display screen 230 of the specimen measurement device 201. Therefore the display screen 230 can be simplified, which leads to reduction of the cost of the specimen measurement device 201.

In addition, outputting the alert tone from the speaker 340 enables the user not watching the display screen 330 to notice the error. Further, causing the communication apparatus 301 to vibrate with the vibrator 350 is advantageous for making the user notice the error, for example when the measurement is performed at a relatively noisy location or when the hearing ability of the user is weakened.

Notifying the user that the temperature measured by the temperature measurement unit 262 is not within the appropriate temperature range is advantageous for preventing inaccurate measurement data from being stored. Notifying the user that the charge amount measured by the charge amount measurement unit 263 is below the charge amount lower limit is advantageous for avoiding such a situation that the specimen measurement device 201 stops working halfway of the measurement. Notifying the user that the time-counting function of the date and time generation unit 264 is not working is advantageous for preventing the measurement data of different date and time from erroneously concentrating to a specific date and time.

Adopting the wireless communication compliant to Bluetooth (registered trademark) standard for transmission and reception of data between the specimen measurement device 201 and the communication apparatus 301 allows the transmission and reception of data therebetween to be automatically started when the measurement device 201 and the communication apparatus 301 are brought into a mutually communicable range, without the need for the user to care about the setting up. The configuration that the specimen measurement device 201 is turned on and off by the insertion and removal of the sensor piece 290 allows the specimen measurement device 201 to be automatically turned on and off in accordance with the intention of the user, by the operation which is in any case mandatory when performing the blood sugar level measurement. These configurations allow the specimen measurement device 201 to start the measurement operation and the communication with the communication apparatus 301 in accordance with the intention of the user, and without the need for the user to take additional care. Further, in the case where the specimen measurement device 201 is in an unsuitable condition for the measurement, the message to that effect is automatically outputted from the communication apparatus 301, in advance of the measurement. Accordingly, the measurement can be smoothly started when the specimen measurement device 201 is in a condition suitable for the measurement, and in case that the specimen measurement device 201 is in a condition unsuitable for the measurement the user can be promptly notified to that effect in advance of the measurement.

Causing the display screen 330 to display the help message corresponding to the error message as shown in FIGS. 7 to 12 allows the user to properly perform the operation for amending the error of the specimen measurement device 201, without depending on the operation manual thereof. Such arrangements are advantageous for alleviating the burden on the user and promptly resetting the specimen measurement device 201 to a condition suitable for the measurement. In addition, the specimen measurement device 201 can be prevented from being broken or suffering a functional defect because of an improper operation that may be committed by the user to amend an error. Further, since the function of displaying the help message is not necessary in the specimen measurement device 201, the cost of the specimen measurement device 201 can be reduced.

Figure 13:
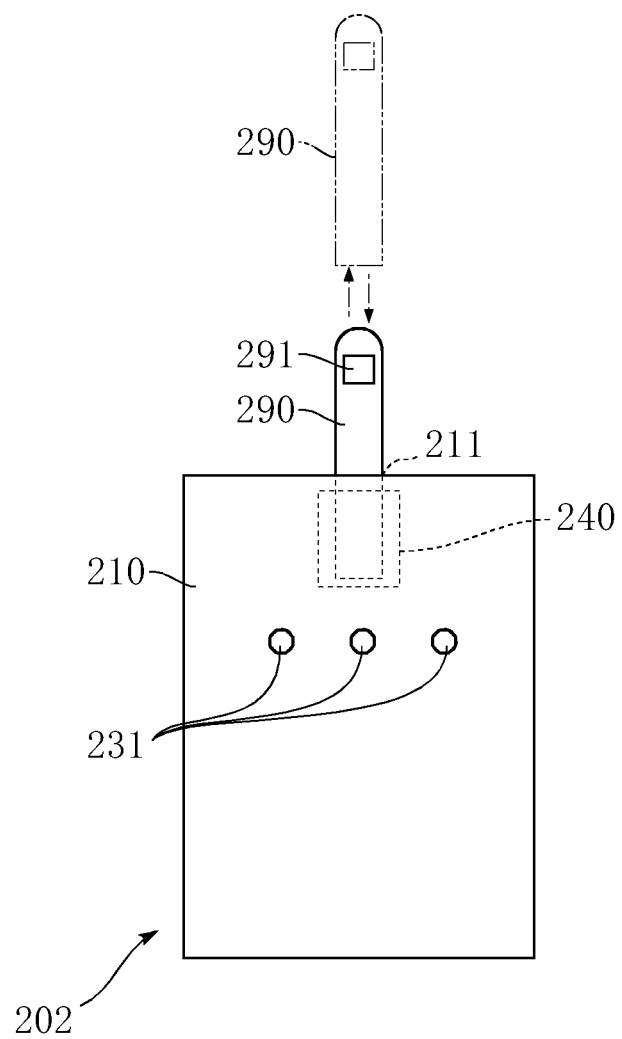
FIG. 13 is a front view showing a specimen measurement device according to a second embodiment of the present invention.
Figure 14:
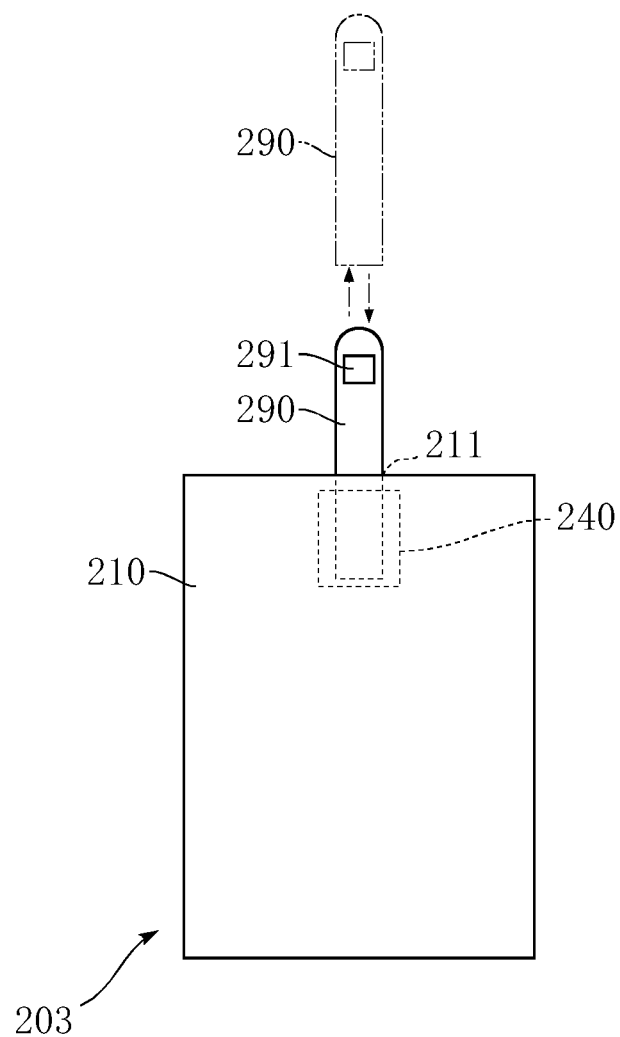
FIG. 14 is a front view showing a specimen measurement device according to a third embodiment of the present invention.
Figure 15:
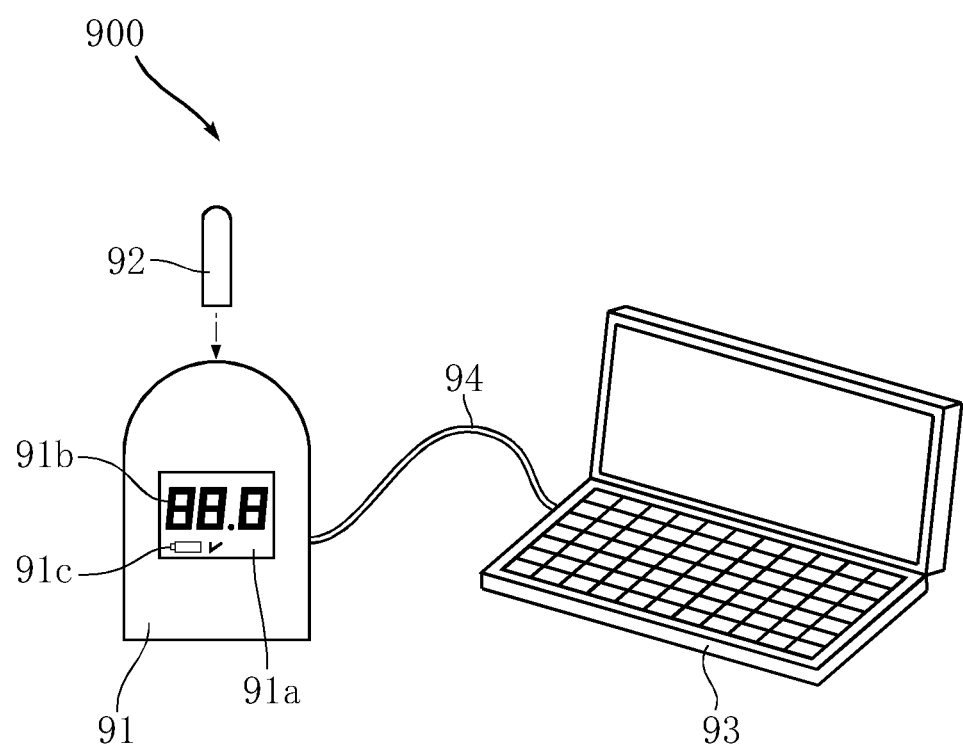
FIG. 15 is a schematic drawing showing a conventional specimen measurement device and a specimen measurement system.

FIGS. 13 and 14 illustrate other embodiments of the specimen measurement device according to the present invention. In these drawings, the constituents same as or similar to those of the foregoing embodiment are given the same numeral.

FIG. 13 illustrates a specimen measurement device according to a second embodiment of the present invention. The specimen measurement device 202 according to this embodiment does not have the display screen 230 as the specimen measurement device 201, but instead includes a plurality of LED indicators 231. The plurality of LED indicators 231 is an example of the measurement device-end display unit according to the present invention. The LED indicators 231 are each configured to output a different color such as green, yellow, or red. For example, the LED indicators 231 are arranged as follows. When the measurement condition decision unit 261 of the control unit 260 decides that the measurement conditions are suitable at the step S34, the control unit 260 turns on the LED indicator 231 of green. In the case where the measurement condition decision unit 261 decides that any one of the measurement conditions is unsuitable, the control unit 260 turns on the LED indicator 231 of red. Further, in the case where such a factor that does not immediately affect the measurement result but may soon incur a malfunction is encountered as a result of the decision by the measurement condition decision unit 261, the control unit 260 turns on the LED indicator 231 of yellow. An example of the factor that may soon incur a malfunction is the situation where a charge amount measured by the charge amount measurement unit 263 is estimated to run out after a few times of measurements.

Such a configuration allows the structure of the specimen measurement device 202 to be further simplified. In this case also, sufficient information can be transmitted to the user by displaying necessary information on the display screen 330 of the communication apparatus 301 through communication.

FIG. 14 illustrates a specimen measurement device according to a third embodiment of the present invention. The specimen measurement device 203 according to this embodiment does not include the display screen 230 as the specimen measurement device 201 nor the plurality of LED indicators 231 as the specimen measurement device 202. In other words, the specimen measurement device 203 does not have the function of displaying the information based on the measurement result given by the measurement unit 220 and the decision results given by measurement condition decision unit 261. The measurement result given by the specimen measurement device 203 and the decision results are displayed on the display screen 330 of the communication apparatus 301 through communication.

Such a configuration eliminates the need to provide the specimen measurement device 203 with a structure for displaying information. Accordingly, the controlling jobs to be performed by the control unit 260 can be simplified, in addition to the advantage that the cost corresponding to the display screen 230 and the plurality of LED indicators 231 can be saved.

The specimen measurement device and the specimen measurement system according to the present invention are in no way limited to the foregoing embodiments. Specific configurations of the constituents of the specimen measurement device and the specimen measurement system according to the present invention may be modified in various manners.

The communication apparatus according to the present invention is not limited to the mobile phone, but may be any apparatus that is capable of performing wireless communication with the specimen measurement device. For example, a personal computer capable of performing transmission and reception of data through wireless communication compliant to Bluetooth (registered trademark) standard may be adopted. The specimen measurement device according to the present invention is applicable not only to the SMBG device, but to various measurement devices from which the measurement data can be collected into or through a communication apparatus. The wireless communication according to the present invention is not limited to the communication compliant to Bluetooth (registered trademark) standard, but may be any communication mode provided that it allows the specimen measurement device and the communication apparatus to perform transmission and reception of data therebetween.

The invention claimed is:
1. A specimen measurement device comprising:
   a measurement unit for measurement of a specific component contained in a specimen;

a measurement condition decision unit that decides suitability of at least one measurement condition required for the measurement and generates measurement condition data containing a decision result on the suitability of the measurement condition;

a data transmitter that transmits the measurement condition data through wireless communication; and a sensor piece detector that detects insertion and removal of a sensor piece, wherein insertion of a sensor piece spotted with the specimen into the specimen measurement device activates the specimen measurement device to measure the specimen, wherein the specimen measurement device is switched, when the sensor piece detector detects the insertion of the sensor piece, to an operative state in which the specimen can be measured from a stand-by state in which the specimen is unable to be measured, wherein the measurement condition decision unit automatically decides the suitability of the measurement condition, after the sensor piece is inserted, wherein the data transmitter automatically transmits the measurement condition data based on the insertion of the sensor piece detected by the sensor piece detector and after the measurement condition decision unit decides the suitability of the measurement condition, and wherein the data transmitter automatically establishes wireless communication after the sensor piece is inserted and before the measurement condition data is transmitted, wherein the communication apparatus includes an improvement remedy storage unit in which improvement remedy data for improving a status of the specimen measurement device on the basis of the measurement condition data is stored, and the communication apparatus-end display unit displays the improvement remedy data together with or after a display of the measurement condition information.

2. The specimen measurement device according to claim 1, further comprising a temperature measurement unit that measures a temperature of a place related to the measurement of the specimen, wherein the measurement condition decision unit decides suitability of the temperature measured by the temperature measurement unit with respect to the measurement of the specimen, and adds the decision result to the measurement condition data as temperature suitability data.

3. The specimen measurement device according to claim 1, further comprising a charge storage unit and a charge amount measurement unit that measures a charge amount in the charge storage unit, wherein the measurement condition decision unit decides suitability of the charge amount measured by the charge amount measurement unit with respect to the measurement of the specimen, and adds the decision result to the measurement condition data as charge amount suitability data.

4. The specimen measurement device according to claim 1, further comprising a date and time generation unit having a clock function so as to identify a date and time of the measurement, wherein the measurement condition decision unit decides suitability of a time-counting status of the clock function of the date and time generation unit with respect to the measurement of the specimen, and adds the decision result to the measurement condition data as time-counting status suitability data.

5. The specimen measurement device according to claim 1, wherein the specific component is blood sugar level.

6. The specimen measurement device according to claim 1, further comprising a measurement device-end display unit that displays at least one of the measurement result of the measurement unit and the decision result of the measurement condition decision unit.

7. The specimen measurement device according to claim 1, wherein the specimen measurement device is provided with no function to display the measurement result given by the measurement unit and the decision result given by the measurement condition decision unit.

8. A specimen measurement system comprising:

the specimen measurement device according to claim 1, and a communication apparatus including a data receiver that receives, through wireless communication, the measurement condition data transmitted from the data transmitter of the specimen measurement device and a communication apparatus-end display unit that displays measurement condition information based on the measurement condition data.

9. The specimen measurement system according to claim 8, wherein measurement data generated by the measurement unit is transmitted from the specimen measurement device by the data transmitter, and the measurement data received by the data receiver is displayed on the communication apparatus-end display unit in the communication apparatus.

* * * * *